USOO5747494A

United States Patent [19]
Medjad et al.

[11] Patent Number: 5,747,494
[45] Date of Patent: May 5, 1998

[54] PHARMACEUTICAL COMPOSITIONS FOR THE TREATMENT OF DEPRESSIVE DISORDERS

[75] Inventors: Nadia Medjad; Martine Billardon, both of Suresnes, France

[73] Assignee: U C B S.A., Brussels, Belgium

[21] Appl. No.: 672,920

[22] Filed: Jun. 28, 1996

[51] Int. Cl.$^6$ .................... A61K 31/495; C07D 241/04
[52] U.S. Cl. .................................... 514/255; 544/396
[58] Field of Search ........................... 514/255; 544/396

[56] References Cited

PUBLICATIONS

Martin et al., "L'Encephale", vol. XXI, Fascicule IV, Jul.–Aug., 1995 pp. 323–324.
Martin et al., European Neuropsychopharmacology, vol. 5, No. 3, Sep., 1995, Abstract P-2-6 pp. 275–276.
Nutt, Journal of Psychopharmacology, vol. 9 (2) Supplement 1995, pp. 185–189.
Den Boer et al., Human Psychopharmacology, vol. 10 (1995) S173–S183.
Lader, British Journal of Psychiatry (1988), vol. 153 (supplement 3).
Angst et al., Psychopharmacology (1992), vol. 106, S109–S113.
Baumhackl et al., British Journal of Psychiatry (1989),I vol. 155 (suppl. 6) pp. 78–83.
Sherman et al., Pharmacology Biochemistry & Behavior, vol. 16, pp. 449–454 (1982).
Martin et al., Pharmacology Biochemistry & Behavior, vol. 24, pp. 177–181 (1986).
Martin et al., Prog. Neuro–Psychopharmacol. & Biol. Psychiat., 1987, vol. 11, pp. 1–7.
Seligman et al., Journal of Experimental Psychology, vol. 74, No. 1, May 1967, pp. 1–9.
Martin et al., Biological Psychiatry (1996), vol. 39, pp. 882–890.
Silver, D. et al.: Hydroxyzine, Amitryptyline and their Combination in the treatment of Psychoneurotic Patients, Curr. Ther. Res., vol. 11, pp. 663–669, 1989.

*Primary Examiner*—C. Warren Ivy
*Assistant Examiner*—Charanjit S. Aulakh
*Attorney, Agent, or Firm*—Wenderoth, Lind & Ponack

[57] ABSTRACT

A method for treating a depressive disorder which comprises administering to a patient in need thereof a therapeutically effective amount of a combination of (i) hydroxyzine, an individual optical isomer thereof, or a pharmaceutically acceptable salt thereof, and
(ii) at least one therapeutic substance which is a serotonin uptake inhibitor, an individual optical isomer thereof or a pharmaceutically acceptable salt thereof.

7 Claims, No Drawings

1

PHARMACEUTICAL COMPOSITIONS FOR THE TREATMENT OF DEPRESSIVE DISORDERS

The present invention relates to pharmaceutical compositions and methods of treatment of diseases in humans. More particularly, the invention relates to combinations of two or more than two pharmaceutical substances as well as to methods of treatment of depressive disorders.

BACKGROUND OF THE INVENTION

Until a few years ago, available antidepressant drugs were tricyclic antidepressants which are known to have a non-selective action on brain monoamines. Recently, more selective antidepressants which are serotonin uptake inhibitors (hereinafter abbreviated SUIs) have been used increasingly due to their better therapeutic index (ratio between efficacy and side-effects)

However, due to their specific type of action, the administration of SUIs presents a number of specific problems. In particular, before the onset of any antidepressant effect, SUIs show a transient increase in nervousness, anxiety and agitation. This problem has been reported for all SUIs (D. NUTT, J. Psychopharmacol. (1995), 9, S 185–189; J. A. DEN BOER, H. G. M. WESTENBERG, Human Psychopharmacol. (1995), 10, S 173–183). Other known problems associated with the administration of SUIs are sleep disorders and insomnia (M. LADER, British J. Psychiatry (1988), 153 (Suppl. 3), 51–58).

Patients who respond to SUI treatment are sometimes considered to show significant improvements in most of their depressive symptoms over time. A number of patients only show a partial response status in which significant residual symptoms persist.

Clearly, the nervousness, anxiety, agitation and sleep disorder dimension of the depressive syndrome is not adequately covered by an SUI treatment. For this reason, it is common practice to use a cotreatment to cover these symptoms (S. KASPER et al., Human Psychopharmacology (1994), 9, 1–12). Among the known cotreatments, the combination of SUIs with benzodiazepines are the most common. For example, in a meta-analysis performed by J. ANGST and M. STABL (Psychopharmacology (1992), 106, 109–113), half of the patients treated with whatever antidepressants were taking a benzodiazepine concomitantly.

However, pharmacological interactions have been observed when antidepressants are administered concomitantly with benzodiazepines. Indeed, a better antidepressive response was observed in patients who were not taking concomitant benzodiazepines when compared to patients who were ( J. ANGST and M. STABL cited above, U. BAUMHACKL et al. British J. Psychiatry (1989), 155 (Suppl. 6), 78–83). In particular, concomitant administration of benzodiazepines and SUIs has been shown in clinical studies to reduce the therapeutic effect of SUIs (E.G. HANTOUCHE et al., L'Encéphale (1995), XXI, 59–65).

Thus, an objective of the present invention is to provide a useful combination of pharmaceutical substance for treating depressive disorders in humans, while avoiding the nervousness, anxiety, agitation and sleep disorders associated with treatments using SUIs, and avoiding at the same time the loss of therapeutic effect observed when treatment with the classic association of SUIs and benzodiazepines is used.

On the other hand, racemic hydroxyzine has been used for a long time for the symptomatic treatment of anxiety. It is also known from U.S. Pat. No. 5,476,941 that one of the enantiomers of hydroxyzine may be used as an anxiolytic or tranquilizing agent for the treatment of diseases which are caused by an excitation of the central nervous system.

SUMMARY OF THE INVENTION

The present invention is based on the unexpected recognition that the combined use of (i) hydroxyzine, an individual optical isomer thereof or a pharmaceutically acceptable salt thereof on the one hand, and (ii) at least one therapeutic substance which is a serotonin uptake inhibitor, an optical isomer thereof, or a pharmaceutically acceptable salt thereof on the other hand, in the treatment of depressive disorders, lacks the negative effects observed when a combination of said therapeutic substance (ii) and benzodiazepines is used.

DETAILED DESCRIPTION OF THE INVENTION

The present invention encompasses a method for treating a depressive disorder which comprises administering to a patient in need thereof a therapeutically effective amount of a combination of (i) hydroxyzine, an individual optical isomer thereof, or a pharmaceutically acceptable salt thereof, and (ii) at least one therapeutic substance which is a serotonin uptake inhibitor, an individual optical isomer thereof or a pharmaceutically acceptable salt thereof.

Therapeutic substances (ii) used according to the invention are serotonin uptake inhibitors. Examples of such therapeutic substances include, but are not limited to, fluoxetine, fluvoxamine, sertraline, indalpine, citalopram, paroxetine or cericlamine.

The term "pharmaceutically acceptable salts" as used herein with respect to hydroxyzine refers not only to its addition salts with pharmaceutically acceptable non-toxic organic and inorganic acids, such as acetic, citric, maleic, succinic, ascorbic, hydrochloric, hydrobromic, sulfuric, and phosphoric acids and the like, but also its metal salts (for example sodium or potassium salts) or ammonium salts.

The term "pharmaceutically acceptable salts" as used herein with respect to the therapeutic substances (ii) means their addition salts with pharmaceutically acceptable non-toxic organic and inorganic acids, such as acetic, citric, maleic, succinic, ascorbic, hydrochloric, hydrobromic, sulfuric, and phosphoric acids and the like, and, if appropriate, also their metal salts or ammonium salts.

The term "individual optical isomer" as used herein means, when the molecule has a center of asymmetry, the levorotatory and the dextrorotatary enantiomers thereof, more precisely, it means that the said compound comprises at least 90%, preferably at least 95%, by weight of the said individual (either dextro- or levorotatory) optical isomer and at most 10% preferably at most 5% by weight of the other individual (respectively levo- or dextrorotatary) optical isomer. Each individual optical isomer ray be obtained by conventional means, i.e., resolution from the corresponding racemic mixture or asymmetric synthesis.

For implementing the method of treatment according to the invention, a therapeutically effective amount of a combination of compounds (i) and (ii) should be administered to the patient. An effective amount can be readily determined by the use of conventional techniques and by observing results obtained under analogous circumstances. In determining the effective amount, a number of factors are considered including, but not limited to; the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; an (the use of concomitant medication.

The doses required according to the present invention should be sufficiently high to permit the relief of depression and its associated nervousness, anxiety, agitation and sleep disorder symptoms.

Administration of a therapeutically effective amount of a combination of compounds (i) and (ii) according to the present invention can be performed simultaneously or separately.

For practical reasons, it may prove preferable to administer compounds (i) and (ii) separately. Since the nervousness, anxiety, agitation and sleep disorder symptoms may change during the treatment, separate administration allows to adapt the doses of compound (i) relative to the doses of compounds (ii) during the treatment.

Optionally, compounds (i) and (ii) may be coadministered with other therapeutically active substances, such as analgesics, antidepressants which are not serotonin uptake inhibitors or any other drug which may prove necessary during therapy.

Another object of the present invention is a pharmaceutical composition comprising a therapeutically effective amount of a combination of (i) hydroxyzine, an individual optical isomer thereof, or a pharmaceutically acceptable salt thereof, and (ii) at least one therapeutic substance which is a serotonin uptake inhibitor, an individual optical isomer thereof or a pharmaceutically acceptable salt thereof.

Pharmaceutical compositions according to the present invention may be administered by any conventional means.

Pharmaceutical compositions intended for oral administration may be solid or liquid, for example, in the form of tablets, pill, dragees, gelatin capsules, sublingual formulations, solutions, syrups, and the like.

For this purpose, the active compounds can be mixed with an inert diluent or a pharmaceutically acceptable non-toxic carrier, such as for example starch or lactose. Optionally, these pharmaceutical compositions can also contain a hinder such as microcrystalline cellulose, gum tragacanth or gelatin, a disintegrating agent such as alginic acid, a lubricant such as magnesium stearate, a glidant such as colloidal silicon dioxide, a sweetening agent such as sucrose or saccharin, a coloring agent or a flavoring agent such as peppermint or methyl salicylate. These compositions also include compositions that allow controlled release of the active substance.

The pharmaceutical forms according to the present invention may be prepared according to conventional methods used by pharmacists.

The percentage of active compound in the pharmaceutical compositions can vary within very wide concentration limits and depends on a variety of factors such as the sex, age, weight and medical condition of the patient, as well as the method of administration.

In the preferred oral compositions, the dosage unit is between 25 mg and 100 mg of active compound (i). The dosage of compounds (ii) depends on which serotonin uptake inhibitors are present in the composition.

As regards the daily dosage, this can vary within a wide range of dosage units. For adults, it is preferably between 25 mg and 100 mg of active compound (i). The daily dosage of compounds (ii) depends on which serotonin uptake inhibitors are present in the pharmaceutical compositions. The daily dosages usually recommended for each serotonin uptake inhibitor is used. For example, in the case of fluoxetine, the daily dosage for adults is preferably between 10 and 80 mg; in the case of fluvoxamine, the daily dosage for adults is preferably between 100 and 200 mg; in the case of sertraline, the daily dosage for adults is preferably between 50 and 200 mg; in the case of citalopram, the daily dosage for adults is preferably between 10 and 60 mg; in the case of paroxetine, the daily dosage for adults is preferably between 20 and 50 mg.

These pharmaceutical compositions according to the present invention are usually administered once or twice a day.

It is to be understood, however, that the specific doses can be adapted for particular cases, depending on individual need, at the discretion of the responsible physician. The above-mentioned dosages are given for exemplary purposes only and by no means limit the scope of practice of the invention.

The following compositions are non-limiting examples of compositions containing compounds (i) and (ii) suitable for oral administration:

| Composition 1 | Composition 2 |
| --- | --- |
| 10 mg fluoxetine.HCl | 10 mg fluoxetine.HCl |
| 25 mg hydroxyzine.2HCl | 100 mg hydroxyzine.2HCl |
| 200 mg lactose | 400 mg lactose |
| 1 mg magnesium stearate | 5 mg magnesium stearate |

The invention is further defined by reference to the following examples describing the utility of compositions according to the present invention, as well as the efficiency of methods of treatment according to the present invention.

1. Learned Helplessness Paradigm

The general approach used in this test consists of inducing a learning deficiency in animals while exposing the said animals to one or several inescapable aversive stimuli. This method has proved effective in demonstrating the antidepressive effect of a large variety of antidepressants in laboratory animals (A. D. SHERMAN et al., Pharmacol. Biochem. Behav. (1982), 16, 449–459, P. Martin et al Pharmacol. Biochem. Behav. (1986), 24, 177–131, ibid, Prog. Neuropsychopharmacol. Biol. Psychiatry (1987), 11 ; 1–7). The technique used in this test, originally developed by M. E. P. SELIGMAN and S. F. MAIER (J. Exp. Psychol. (1967), 74, 1–9) comprises essentially two stages. 1st stage (day 1): rats are placed in small plexiglass boxes (20×20×10 cm) with a floor made of a metallic grid through which current may pass. The rats are then submitted to 60 inescapable 0. 2 mA shocks lasting 15 seconds, produced every minute in random areas of the grid. Control animals are placed during one hour in identical boxes without current passing through the metallic grid (non-helpless control group). 2nd stage: conditioning sessions:

48 hours after the first stage (day 3), the animals are placed one by one in one of the compartments of an automated plexiglass "shuttle box" (60×21×30 cm). The shuttle boxes are divided in two compartments, separated by a wall perforated by a 7 ×7 cm hole and possess a floor which is a metallic grid through which current may pass. A photoelectric system stops the current flow when the animal changes compartments.

After five minutes without any movement constraint, the animals are subjected during 15 minutes to 30 tests lasting 30 seconds each.

During the first three seconds of each test, a visual stimulus is presented to the animal, followed by an electric shock which lasts 3 seconds (0. 8 mA) during which the visual stimulus is still present, followed itself by rest periods of 24 seconds. The expected response is that the animal changes compartments, either when it sees the visual stimulus or when it feels the shock. Failure to escape is considered when the rat hasn't changed compartments and takes the full three seconds long electric shock. According to previous studies on this test, it is the number of escape failures which is considered in order to compare various groups with one another.

Conditioning sessions are repeated on day 4 and day 5.

The animals used in this test are male Wistar AF rats. Using this test, the activities of hydroxyzine dihydrochloride, fluoxetine hydrochloride and fluvoxamine hydrochloride, each administered alone, and the activities of fluoxetine hydrochloride and fluvoxamine hydrochloride each coadministered with hydroxyzine dihydrochloride were studied.

The compounds are administered by intraperitoneal injection (0.5 ml/100 mg rat). Control animals received distilled water (0.5 ml/100 g rat, helpless control group).

The animals on which the test was performed were treated during 5 consecutive days. On day 1, the active ingredients were administered in one administration, 6 hours after the inescapable shocks. On days 2 to 5, the daily doses of active ingredients were administered in two half doses administered in the morning and in the evening respectively.

Table 1 gives for each compound or combination of compounds tested the daily dose of active ingredients, the number of rats treated and the mean number of escape failures per 30 trials (±S.E.M.).

Statistical analysis of the results was performed in the following way: inter-group comparisons were performed by ANOVA (analysis of variance); intra-group comparisons were performed using Dunnett's or Dunn's tests. All tests were two-tailed. All the results presented in Table 1 are considered to be statistically significant for a risk factor $\alpha=0.05$.

In another study using exactly the same test performed under similar conditions, (P. MARTIN and A. PUECH, Biological Psychiatry (1996), Vol. 39, pages 882–890), the activities of several serotonin uptake inhibitors coadministered with benzodiazepines were studied. For comparison purposes, results which are relevant in the present context are shown in Table 2.

TABLE 1

Learned Helplessness Paradigm (fluoxetine, fluvoxamine and hydroxyzine)

| Compound tested-daily dosage | No. of rats tested | Mean number of escape failures ± SEM | | |
|---|---|---|---|---|
| | | day 3 | day 4 | day 5 |
| None; non-helpless control | 12 | 9 ± 2 | 8 ± 2 | 11 ± 3 |
| None; helpless control | 12 | 21 ± 2 | 23 ± 2 | 26 ± 2 |
| hydroxyzine.2HCl-8 mg/kg | 12 | 15 ± 3 | 20 ± 3 | 17 ± 3 |
| fluoxetine.HCl-4 mg/kg | 12 | 13 ± 1 | 14 ± 2 | 14 ± 3 |
| fluvoxamine.HCl-4 mg/kg | 12 | 15 ± 2 | 15 ± 3 | 13 ± 3 |
| hydroxyzine.2HCl-8 mg/kg; fluoxetine.HCl-4 mg/kg | 12 | 21 ± 1 | 15 ± 2 | 18 ± 3 |
| hydroxyzine.2HCl-8 mg/kg; fluvoxamine.HCl-4 mg/kg | 12 | 15 ± 3 | 14 ± 3 | 15 ± 3 |

TABLE 2

Learned Helplessness Paradigm. (fluvoxamine, lorazepam and diazepam)*

| Compound tested-daily dosage | No. of rats tested | Mean number of escape failures ± SEM | | |
|---|---|---|---|---|
| | | day 3 | day 4 | day 5 |
| none; non-helpless control | | | 5 to 10 | |
| none; helpless control | | | 18 to 22 | |
| fluvoxamine.HCl-4 mg/kg | 10 | 11 ± 1 | 8 ± 2 | 6 ± 1 |
| lorazepam-0.125 mg/kg; fluvoxamine.HCl-4 mg/kg | 10 | 21 ± 2 | 22 ± 1 | 19 ± 2 |
| diazepam-1 mg/kg; fluvoxamine.HCl-4 mg/kg | 10 | 16 ± 2 | 15 ± 3 | 16 ± 3 |

*For comparison purposes; P. MARTIN and A. PUECH, Biological Psychiatry (1996), Vol. 39, Pages 882–890.

Table 1 shows that animals in the non-helpless control group cannot escape the electric shocks in about 30% of the cases on day 3 (9 ±2 escape failures out of 30 trials). The mean number of escape failures remains stable on days 4 and 5.

In contradistinction, for the animals in the helpless control group, the mean number of escape failures very high and tends to increase on days 4 and 5.

For the animals treated with hydroxyzine dihydrochloride, Table 1 shows that hydroxyzine dihydrochloride tends to reduce the behavioral deficit caused by the inescapable shocks of day 1. This effect is not significant on days 3 and 4 (p=0.12 and 0.40 respectively), but becomes significant on day 5 (p=0.002).

Table 1 also shows that fluvoxamine hydrochloride results in a significant reduction of the mean number of escape failures (p≦0.006 for all results with fluoxetine hydrochloride; p=0.1 on day 3, p=0.09 on day 4 and p=0.004 on day 5 for fluvoxamine hydrochloride). Fluoxetine hydrochloride gives, for each group of rats tested, the daily dosage used, the number of rats treated and the mean number of activity impulsions (±SEM) for each period of 5 minutes.

Statistical treatment of the results was performed by two-tailed variance analysis.

Hydroxyzine dihydrochloride was administered intraperitoneally. A group of control animals was given an isotonic solution.

Table 3 shows that hydroxyzine dihydrochloride administered at a daily dosage of 8 mg/kg does not affect the spontaneous motor activity of the rats tested.

The learned helplessness test results presented in Table 1 are thus significant.

TABLE 3

| | | Spontaneous Motor Activity. | | | | | |
|---|---|---|---|---|---|---|---|
| | No. of | Mean number of activity impulsions Time (minutes) | | | | | |
| Compound tested - Daily dosage | rats | 5 | 10 | 15 | 20 | 25 | 30 |
| Control (NaCl) | 10 | 712 ± 21 | 577 ± 39 | 433 ± 52 | 457 ± 33 | 378 ± 37 | 245 ± 67 |
| Hydroxyzine.2HCl- 8 mg/kg | 11 | 716 ± 17 | 631 ± 32 | 513 ± 55 | 454 ± 73 | 282 ± 70 | 265 ± 81 | and fluvoxamine hydrochloride thus clearly produce an antidepressant effect.

When fluoxetine hydrochloride is coadministered with hydroxyzine dihydrochloride, an antidepressant effect is still observed, especially on day 5 of the treatment.

When fluvoxamine hydrochloride is administered with hydroxyzine dihydrochloride, an antidepressant effect similar to the effect obtained when fluvoxamine hydrochloride is administered alone is achieved.

On the other hand, the results of the previous study presented in Table 2 show that when fluvoxamine hydrochloride is coadministered with lorazepam or diazepam at the daily dosages of 0.125 mg/kg and 1 mg/kg, respectively, the mean number of escape failure becomes identical to the mean number of escape failures of the helpless control group.

The escape deficit induced by inescapable shocks was thus not reduced in rats treated with benzodiazepines.

Tables 1 and 2 thus clearly show that coadministration of fluoxetine hydrochloride or fluvoxamine hydrochloride with hydroxyzine dihydrochloride allows to reduce significantly the mean number of escape failures, whereas such a result cannot be achieved when fluvoxamine hydrochloride is coadministered with a benzodiazepine.

2. Motor Activity

In order to check whether the results on the mean number of escape failures could be validly interpreted in terms of an antidepressant effect, the following test on spontaneous motor activity was performed.

Male wistar AF rats are treated with hydroxyzine dihydrochloride at the daily dosage of 8 mg/kg, and are tested in the same conditions as those used for the learned helplessness paradigm test, except that the animals do not receive the inescapable electric shocks. On day 5, and after receiving the last dose of active compounds, each animal is placed for 30 minutes on the platform of an actimeter, in order to measure its spontaneous motor activity. The actimeters use magnetic field inducers and are thus capable of recording any movement, even very small.

The number of activity impulsions is recorded for periods of 5 minutes, during a total period of 30 minutes. Table 3

We claim:

1. A method for treating a depressive disorder which comprises administering to a patient in need thereof a therapeutically effective amount of a combination of (i) hydroxyzine, an individual optical isomer thereof, or a pharmaceutically acceptable salt thereof, and (ii) at least one therapeutic substance which is a serotonin uptake inhibitor selected from the group consisting of fluoxetine, fluvoxamine, between fluoxetine and fluvoxamine an individual optical isomer thereof or a pharmaceutically acceptable salt thereof.

2. A method according to claim 1 wherein compounds (i) and (ii) are administered separately.

3. A method according to claim 1 wherein compounds (i) and (ii) are administered simultaneously.

4. A method according to claim 1 wherein compounds (i) and (ii) are administered orally.

5. A pharmaceutical composition comprising a therapeutically effective amount of a combination of (i) hydroxyzine, an individual optical isomer thereof, or a pharmaceutically acceptable salt thereof, and (ii) at least one therapeutic substance which is a serotonin uptake inhibitor selected from the group consisting of fluoxetine, fluvoxamine, between fluoxetine and in, an individual optical isomer thereof or a pharmaceutically acceptable salt thereof.

6. A pharmaceutical composition according to claim 5 wherein the daily dosage of active compound (i) is between 25 and 100 mg per day.

7. A pharmaceutical composition according to claim 5 which further comprises pharmaceutically acceptable solid or liquid diluents or carriers therefor.

* * * * *